United States Patent [19]
Layton

[11] 4,187,722
[45] Feb. 12, 1980

[54] DEVICE FOR MEASURING THE VELOCITY OF A URINE DISCHARGE

[75] Inventor: Terry N. Layton, Wheeling, Ill.

[73] Assignee: The Kendall Company, Boston, Mass.

[21] Appl. No.: 889,153

[22] Filed: Mar. 22, 1978

[51] Int. Cl.² ............................ A61B 5/00; G01F 1/06
[52] U.S. Cl. ....................................... 73/229; 73/195;
73/215; 128/295; 128/771
[58] Field of Search ............... 73/215, 228, 229, 195;
128/2 F, 295

[56] References Cited

U.S. PATENT DOCUMENTS

| 57,580 | 8/1866 | Schnebly | 73/229 X |
|---|---|---|---|
| 1,265,420 | 5/1918 | Bieber | 73/229 X |
| 2,648,981 | 8/1953 | Drake, Jr. | 128/2 |
| 3,406,570 | 10/1968 | White | 73/229 |
| 3,531,988 | 10/1970 | Casani et al. | 73/187 |
| 3,636,766 | 1/1972 | Austin | 73/228 |
| 3,859,854 | 1/1975 | Dye | 73/215 |
| 4,085,616 | 4/1978 | Patel | 128/2 X |

FOREIGN PATENT DOCUMENTS 929398 6/1955 Fed. Rep. of Germany ............ 73/229

*Primary Examiner*—Herbert Goldstein
*Attorney, Agent, or Firm*—Powell L. Sprunger

[57] ABSTRACT

A device for measuring a urine discharge comprising, a hollow receptacle having an inlet port adjacent an upper end of the receptacle and a channel below the inlet port to receive the liquid passing through the inlet port. The device measures the velocity of the discharge passing from the port to the channel.

13 Claims, 5 Drawing Figures

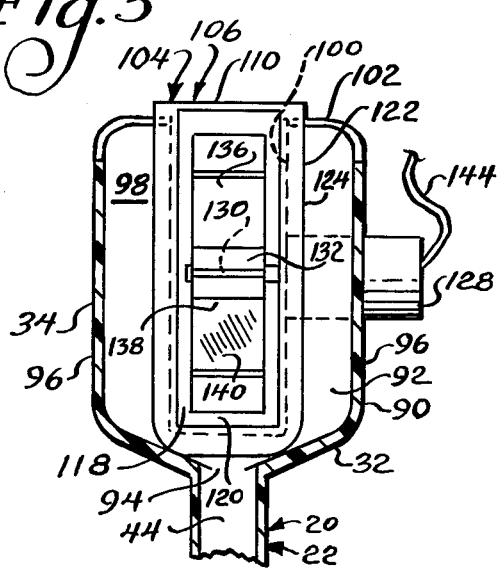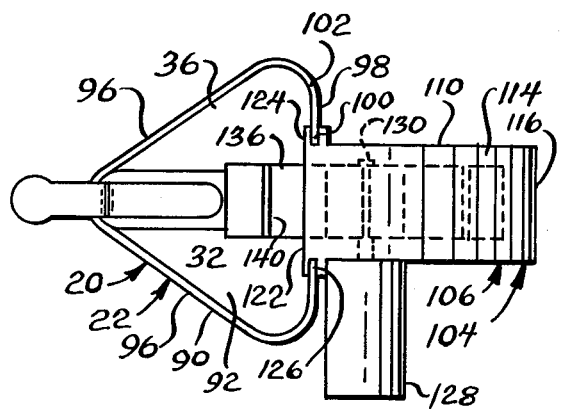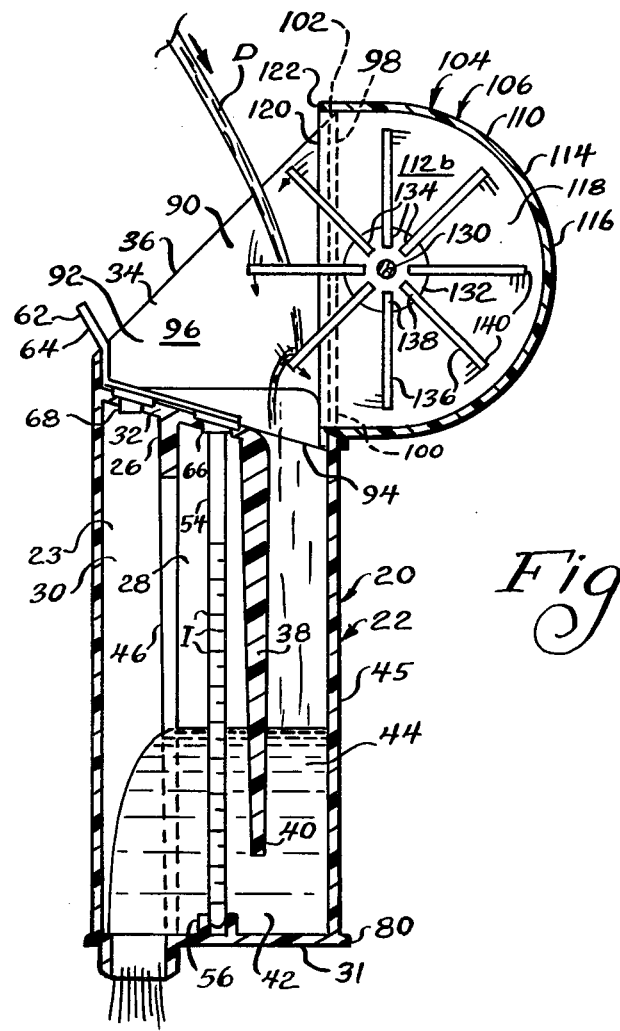

DEVICE FOR MEASURING THE VELOCITY OF A URINE DISCHARGE

BACKGROUND OF THE INVENTION

The present invention relates to a device for measuring a discharge of urine.

In the past, it has been desirable to obtain various data pertaining to a urine discharge. In particular, it was discovered that many urological problems could be readily diagnosed by analyzing information obtained during the natural voiding of urine by patients. For example, the velocity of the urine discharge is affected by the anatomical location of a stricture in the patient, and the peak flow rate and velocity of the urine discharge may be utilized for the purpose of identifying and locating such a condition in the patient. Presently, various types of devices are utilized to obtain data on the urine stream which, in general, have suffered from less than total reliability, and have been rather bulky and somewhat difficult to use.

SUMMARY OF THE INVENTION

A principal feature of the present invention is the provision of a device of simplified construction for measuring a discharge of urine.

The device of the present invention comprises, a hollow receptacle having a sidewall defining inlet port means adjacent an upper end of the receptacle, and channel means below the inlet port means to receive the discharge passing through the port means. The device has a paddle assembly received in a back portion of the sidewall, with the assembly having a rotatable shaft, and a plurality of blades extending radially from and spaced circumferentially around the shaft with outer end portions of the blades located in the path of the discharge. The device has means for generating a signal responsive to rotation of the shaft, and means for measuring the signal.

A feature of the present invention is that the incoming discharge causes rotation of the blades and shaft.

Thus, another feature of the invention is that the discharge and rotating shaft cause a signal to be generated which is measured by the device.

Still another feature of the invention is that the measured signal provides an indication of the velocity of the discharge passing into the receptacle.

Yet another feature of the invention is that the device is capable of measuring the maximum velocity of the discharge.

A further feature of the invention is that the device measures the peak flow rate and volume of the discharge.

A feature of the invention is that the data obtained by the device may be utilized to diagnose a patient.

Another feature of the invention is that the device may be self-administered by the patient during use.

Further features will become more fully apparent in the following description of the embodiments of this invention and from the appended claims.

DESCRIPTION OF THE DRAWINGS

In the drawings:

FIG. 3 is a fragmentary sectional view taken substantially as indicated along the line 3—3 of FIG. 2;

FIG. 4 is a top plan view of the device of FIG. 2; and

FIG. 5 is a sectional view of the device of FIG. 2 illustrating use of the device to measure a urine discharge.

DESCRIPTION OF THE PREFERRED EMBODIMENTS

Figure 1:
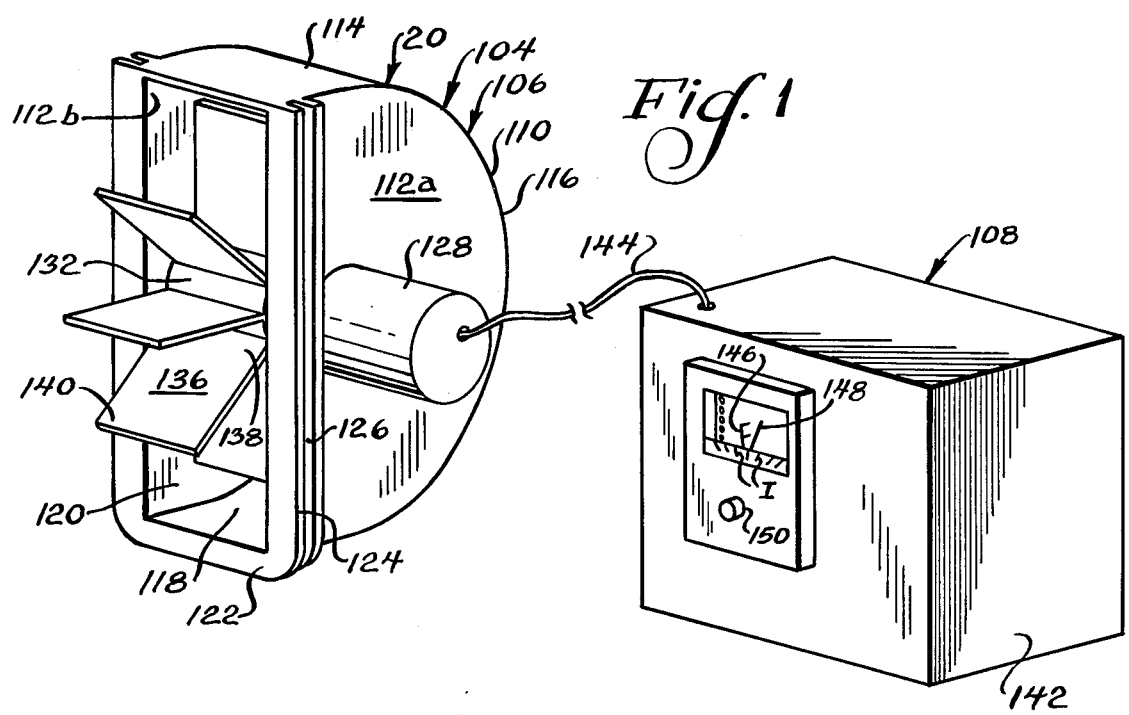
FIG. 1 is a fragmentary perspective view illustrating part of a urine measuring device of the present invention.

Referring now to FIGS. 1–5, there is shown a device generally designated 20 for measuring and collecting a discharge of liquid, such as urine. The device 20 includes a hollow receptacle generally designated 22 having a cavity 23, and a container designated generally 24 having an upper end 25 releasably attached to a lower end 27 of the receptacle 22. Preferably, the receptacle 22 is made from a suitable transparent material, such as plastic.

The receptacle 22, which has rounded end portions and an elongated central portion, has an upright wall 26 which extends laterally across the inside of the receptacle and which extends vertically substantially the height of the receptacle. The upright wall 26 separates the inside of the receptacle into a compartment 28 and a passageway or channel 30. The lower end of the compartment 28 is closed by a bottom wall 31, while the upper end of the passageway 30 and compartment 28 is partially covered by an upper wall 32.

The receptacle 22 has an enlarged portion 34 adjacent an upper end of the receptacle defining an inlet port or opening means 36 to receive the incoming urine discharge, as indicated by the direction of the arrows in FIG. 5. The receptacle has a wall 38 extending laterally across the inside of the receptacle, and having a lower end 40 defining a space 42 intermediate the lower end 40 of the wall 38 and the lower or bottom wall 31 of the receptacle. The wall 38 partially defines the compartment 28 and a channel or channel means 44 intermediate the wall 38 and an outer sidewall 45 of the receptacle 22. Thus, the urine discharge passes from the port 36 through the channel means 44 and space 42 into the compartment 28.

Figure 2:
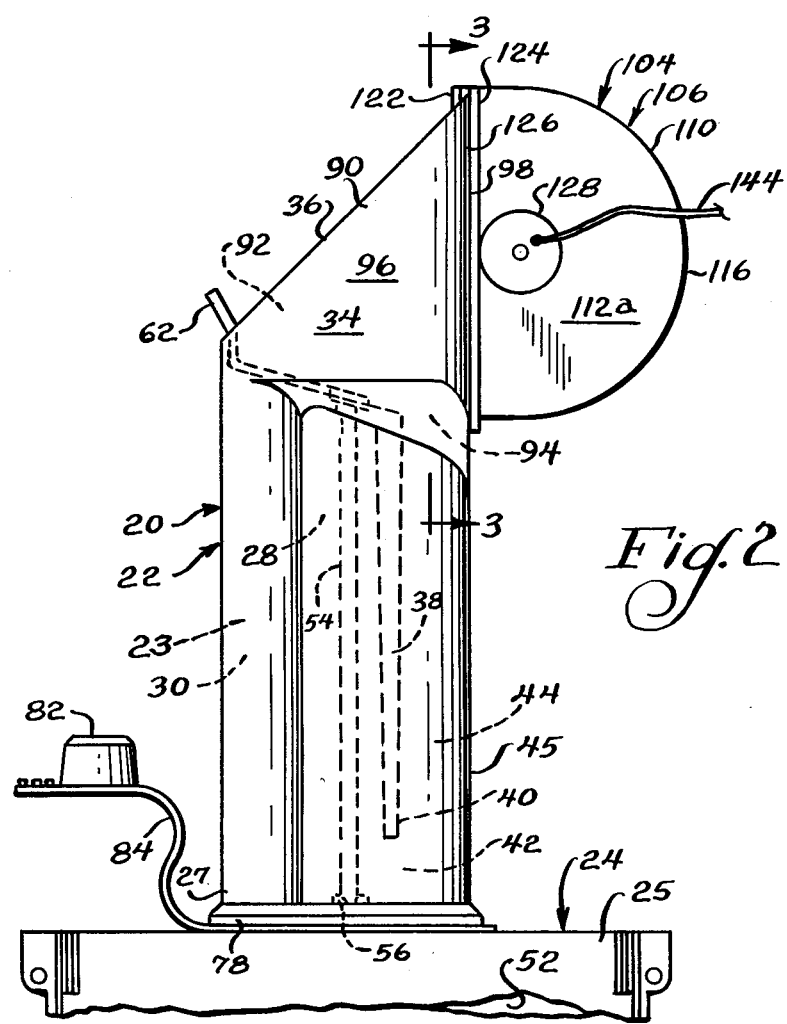
FIG. 2 is a fragmentary elevational view of the device of the present invention.

The wall 26 has an elongated vertical slot or opening means 46 communicating between the compartment 28 and the passageway means 30 to permit passage of the liquid from the compartment to the passageway means and into a chamber 52 in the container 24. As shown in FIGS. 2 and 5, an indicating strip 54 is removably inserted into the compartment 28, with retaining means 56 adjacent the lower end 27 of the receptacle releasably receiving a lower end of the indicating strip 54. As best shown in FIG. 5, the retaining means 56 has a pair of bosses extending from the bottom wall 31 into the cavity 23, with the bosses defining a slot which receives the lower end of the strip 54 and assists in retaining the strip 54 in an upright position in the compartment 28.

As shown in FIG. 5, a retaining member 62 has an elongated flexible tab 64 having first and second spaced plugs 66 and 68, respectively, extending outwardly from one surface of the tab 64, with the first plug 66 being located adjacent one end of the tab 64 and the other plug 68 being located intermediate the plug 66 and the other end of the tab. The first plug 66 has a slot to receive and retain an upper end of the indicating strip 54. The upper wall 32 has a first opening communicating with the compartment 28 to receive the indicating strip 54 and first plug 66, with the first opening having dimensions to snugly engage the first plug 66. The upper wall 32 also has a second opening extending through the wall to snugly receive the second plug 68. Thus, the first and second plugs 66 and 68 are removably received in the first and second openings to releasably retain the tab 64 in place above the upper wall 32, while the first plug 66 assists in retaining the upper end of the indicating strip 54 in an upright position in the compartment 28. As shown in FIGS. 2 and 5, the outer end of the tab 64 extends past the enlarged portion 34 to facilitate removal of the retaining member 62 from the receptacle 22.

The indicating strip 54 is sensitive to contact or wetting by liquids, such as urine, and provides an indication of the maximum height of liquid reached in the compartment 28 during the liquid discharge. Any suitable material may be utilized for the indicating strip 54, such as a material which changes color upon contact by the liquid. For example, a methylene blue compound or rhodamine may be utilized on the strip 54 to obtain the color contrast desired. Preferably, the indicating strip 54 is utilized a single time to measure the height of liquid in the compartment 28. Thus, the retaining member 62 permits easy placement and removal of indicating strips 54 in the receptacle 22. After removal of the strips, flow rate information may be determined by suitable indicia I' spaced along the strip. If desired, the strip may be discarded after it has been removed and the information determined. Alternatively, if it is desired to keep the strip for a later reading, the other end of the tab 64 may be placed in a clip (not shown), or the second plug 68 may be positioned in an opening of a retaining device (not shown) to retain the strip until it is read. In either event, the retaining member 62 permits handling of the strip 54 in a sanitary manner without contacting the strip with the user's hands.

As shown in FIGS. 2 and 5, the container 24 has an upper resilient support member 78 which is releasably attached to a flange 80 at the lower end 27 of the receptacle 22. The support member also includes a closure plug 82 attached to the support member 78 by a strap 84. The plug 82 is removably received in an opening of the support member 78 when the container 24 is removed from the receptacle 22. As shown, the container 24 has a pair of flexible sidewalls depending from the support member 78 and defining the chamber 52. The container sidewalls may be made of any suitable material, preferably transparent, such as polyethylene, and one of the sidewalls may have a plurality of vertically spaced indicia to measure the volume of liquid collected in the chamber 52.

With reference to FIGS. 2-5, the enlarged portion 34 of the receptacle 22 has a sidewall 90 defining a cavity 92 which communicates between the port 36 and an opening 94 at the upper end of the channel 44. The sidewall 90 has a pair of side portions 96 and a back portion 98 connected to the side portions 96. The back portion 98 of the sidewall 90 has a cutout or slot 100 extending downwardly from an upper edge 102 of the back portion 98.

With reference to FIGS. 1-5, the device 20 has a velocity measuring apparatus generally designated 104 having a paddle assembly 106 and a measuring instrument 108. The paddle assembly 106 has a housing 110 having a pair of spaced semi-circular side plates 112a and 112b, and an elongated curved cover plate 114 connected to edges of the side plates 112a and b and closing a back end 116 of the housing 110, with the plates 112a and b and cover plate 114 defining a cavity 118 which communicates with an opening 120 at a front end 122 of the housing 110. The housing also has a U-shaped flange 124 extending around the sides and lower part of the housing 110 at the front end 122 of the housing. The flange 124 defines a slot 126 to receive the side margins of the sidewall back portion 98 which extend peripherally around the slot 100, such that the housing 110 may be releasably attached to the sidewall 90 with the back portion sidewall margins received in the housing slot 126. Thus, the housing 110 may be readily attached to and disconnected from the enlarged portion 34 by placement and removal of the housing relative to the receptacle slot 100. If desired, the housing 110 may be removed from the enlarged portion 34, and a suitable plate (not shown) may be placed in the open part of the back portion 98 to close the slot 100.

The apparatus 104 has a direct current motor/generator 128 connected to the sidewall 112a of the housing 110, with the generator 128 having a rotatable shaft 130 extending into the cavity 118 of the housing 110. The shaft 130 has a cylindrical stem 132 received on the shaft 130 in the cavity 118, with the stem 132 having a plurality of transverse slots 134 equally spaced circumferentially around the stem 132 and shaft 130. The assembly 106 has a plurality of elongated blades 136 having a width slightly less than the width of the cavity 118, and a length less than the distance between the shaft and the cover plate 114. As shown, inner ends 138 of the blades 136 are received in the stem slots 134, and the blades 136 have a sufficient length such that outer ends 140 of the blades 136 project through the housing opening 120 into the receptacle cavity 92 when the blades are aligned with the opening 120. Thus, as the shaft 130 rotates in the housing, the rotating blades 136 progressively project out of the housing and then pass into the housing cavity 118. In a suitable form, as shown, the assembly 106 may have eight blades 136 equally spaced circumferentially around the shaft 130. Of course, the outer ends 140 of the blades 136 are spaced from the cover plate 114 when the blades are located in the housing cavity 118.

The measuring instrument 108 may be of any suitable type, such as an ammeter 142 which is connected to the generator 128 by a suitable lead of conductor 144. The ammeter 142 may have a first movable needle 146 which indicates the instantaneous magnitude of the current generated by the generator 128. Further, the ammeter 142 may have a second needle 148 which is carried by the first needle 146 in a direction associated with an increase in current, e.g., clockwise, but remains stationary when the first needle 146 moves in an opposed direction associated with a decrease in current, e.g., counterclockwise, such that the second needle 148 provides an indication of the maximum amount of current during a period of time or a particular test. After the test has been completed, the needle 148 may be reset to a zero of null condition through use of a suitable knob 150. The ammeter 142 may also have a plurality of indicia I associated with the needles 146 and 148 for a purpose which will be described below. In a preferred form, the magnitude of the current generated by generator 128 is directly proportional to the angular velocity of the shaft 130.

With reference to FIGS. 1 and 5, as the urine discharge D passes through the port 36 into the receptacle, the discharge D strikes the outer ends 140 of the blades 136 which are located in the path of the incoming discharge D. Thus, the discharge D causes the blades 136 to move and rotate about the axis of the shaft 130, such that the generally linear motion of the discharge D is translated by the device into angular motion of the blades and shaft which is directly proportional to the discharge velocity. In turn, the rotating shaft 130 causes the generator 128 to form a signal or current which is transmitted over lead 144 to the ammeter 142, with the magnitude of the signal being directly proportional to the angular velocity of the shaft and linear velocity of the discharge. As a result, the needles 146 and 148 of the ammeter 142 are deflected in a manner providing an indication of the current and associated velocity of the discharge D. Thus, the indicia I on the ammeter 142 may be suitably calibrated to provide a direct indication of the velocity of the discharge D in conjunction with the needles, such that the first needle 146 provides an indication of the instantaneous discharge velocity, while the second needle 148 provides an indication of the maximum discharge velocity. Accordingly, the first needle 146 may be utilized to determine the velocity profile of the discharge during voiding, while the second needle 148 may be utilized to determine the maximum velocity of the discharge D after voiding has been completed. In a preferred form, the lead 144 of the device has a sufficient length such that the ammeter 142 may be placed at a location outside a room where the receptacle 22 and a patient are located. Thus, the patient may utilize the device in complete privacy while the ammeter is checked by a physician or nurse.

In use of the device, the second needle 148 is reset by the knob 150 to the null position, the plug 82 of the container 24 is removed from the opening of the support member 78, and the support member 78 of the container 24 is attached to the lower end 27 of the receptacle 22. The port 36 of the receptacle 22 is then positioned by the patient in privacy to receive the discharge of urine. As the liquid discharge passes into the enlarged portion 34 of the receptacle 22, the discharge D impinges upon the outer ends 140 of the blades 136 causing rotation of the blades and generation of current by the generator 128, thus resulting in an indication of the discharge velocity by the ammeter 142 in a manner as previously described. Further, as the blades 136 rotate, the discharge D passes by the blades and through the opening 94 into the channel 44 of the receptacle 22. Due to the relatively free rotation of the shaft and blades, the paddle assembly 106 has minimal effect upon the dynamic characteristics of the incoming discharge D as it passes into the channel 44 in order to minimize the effect upon a determination of the discharge peak flow rate. The discharge D then passes from the channel 44 and collects in a lower part of the compartment 28, after which it passes from the compartment 28 through the slot 46 into the passageway 30. From the passageway 30 the liquid flows into the chamber 52 of the container 24 for collection therein.

As the rate of discharge into the receptacle increases, the height of liquid in the compartment 28 also increases while the liquid also drains through the slot 46 into the passageway 30. For a given rate of flow of the discharge into the receptacle the liquid attains a fixed height in the chamber, while the liquid passes at a fixed predetermined rate of flow through the slot 46. Hence, if the rate of flow of the liquid discharge into the receptacle is greater than the predetermined exit rate, the height of liquid in the chamber increases, and as long as the rate of flow of the discharge into the receptacle continues to increase, the height of liquid in the compartment 28 continues to rise, and the rate of flow of liquid through the slot 46 also increases. When the flow rate of the incoming discharge abates, the liquid drains from the compartment 28 into the passageway 30 faster than it enters the compartment, and the height of the liquid in the compartment begins to subside.

Peak flow rate of the incoming liquid discharge may be defined as the maximum rate of flow of the discharge. Since the height of liquid in the compartment raises or lowers responsive to an increase or decrease, respectively, of the flow rate of the incoming discharge, it is apparent that the maximum height of liquid attained in the compartment during the discharge serves as an indication of the approximate peak flow rate of the discharge. Although anomalies in the discharge, such as a momentary surge of the discharge, may not be ultimately reflected in the maximum liquid height in the compartment, due, in part to the lag between the time the discharge enters the receptacle and the time it enters the compartment, the device determines the peak flow rate with sufficient accuracy for such purposes as are under discussion. In particular, a urine stream during voiding has a relatively slow rate of change of flow rate, and the device of the present invention indicates a peak flow rate for the discharge which is sufficiently accurate for purposes of diagnosing the patient.

It is possible that the approximate peak flow rate of the urine discharge may be determined by observing the highest level of liquid accumulated in the compartment 28 during the discharge. Direct reading by the patient may be impractical or difficult during self-administration of the apparatus as thus far described, if the apparatus is utilized to collect a discharge of liquid during voiding, and it is desirable that the device be self-administered by the patient in order to alleviate any psychological problems of the patient which might be caused by observation of the receptacle during voiding.

Accordingly, the indicating strip 54 has been provided to automatically record the approximate maximum height of liquid collected in the compartment 28 during the liquid discharge. After the liquid discharge has been completed, a direct reading of the approximate peak flow rate may be determined by the indicia I', either before or after removal of the indicating strip 54 from the receptacle 22. Alternatively, the indicia I' may be placed on the wall of a transparent receptacle 22.

It is apparent that the rate of drainage from the compartment 28 into the passageway 30 is partly dependent upon the precise structure of the receptacle 22. For example, although the slot 46 is shown as having parallel sides, it is contemplated that the slot may be widened or narrowed at desired vertical positions to increase or decrease the flow rate of liquid through the wall in that area, and the wall 26 may have a plurality of slots or openings if desired. Also, the cross sectional area of the compartment 28 itself may be selected of a suitable size to provide the desired sensitivity of liquid column height for a more accurate determination of the peak flow rate.

It is contemplated that a particular structure for the receptacle would first be established, dependent on the accuracy desired and the expected range of values for the peak flow rate of the liquid discharge. Next, the receptacle could be calibrated against known constant flow rates of a discharge passing into the receptacle to determine the appropriate location of the indicia I' on the strip. That this may be readily accomplished is apparent from the fact that the peak flow rate for a discharge having a constant flow rate is the value of the constant flow rate itself. Accordingly, when the discharge of constant flow rate is directed into the receptacle, liquid rises in the compartment to a level at which liquid entering the compartment is offset by the liquid draining from the compartment into the channel, and the receptacle or strip is marked at this height for peak flow rate by the value of the flow rate of the constant discharge.

As noted above, once the rate of flow of the liquid discharge into the receptacle abates, the height of the liquid in the compartment 28 subsides, and the approximate peak flow rate has already been determined on the indicating means or strip 54. During the remainder of the liquid discharge, the liquid continues to drain from the compartment 28 into the passageway 30 until the discharge is terminated and drainage from the compartment to the channel eventually stops. Since the liquid drains from the passageway 30 of the receptacle 22 into the container 24, the volume of liquid which collects in the container 24 during the liquid discharge may be readily determined by the indicia on the container 24.

Since the patient may use the device without observation, unnatural voiding or failure to void which commonly occur when a patient voids under observation is prevented. As previously discussed, the physician may determine the instantaneous velocity of the discharge through use of the ammeter at a remote location during voiding by the patient. After voiding, the physician may determine the maximum velocity of the discharge by the ammeter, and the receptacle 22 may be used to further diagnose the patient's voiding. As previously indicated, the indicating strip 54 may be removed from the receptacle to obtain a reading of the peak flow rate of the urine discharge by use of the indicia I' on the strip 54, or the strip may be retained for later use if desired. The container 24 may be removed from the receptacle 22 to obtain a specimen of urine from the chamber 52 of the container 24 through the container opening. Alternatively, the closure plug 82 may be placed in the container opening to close the opening and cavity 52 of the container 24, and the specimen may be retained for later use, if desired. In either event, the closed container 24 may be discarded in a sanitary manner after removal from the receptacle 22. The receptacle 22 may be cleaned and sterilized for future use with a different indicating strip 54, to reduce the cost of diagnosing various patients.

Thus, the instantaneous and maximum velocity of the discharge D may be readily determined by the indicia I on the ammeter 142, and the peak flow rate of the discharge may be determined by the indicating strip 54. Further, the total volume of the discharge collected in the chamber 52 of the container 24 may be readily determined through use of suitable indicia on the side walls of the container 24. If desired, the container 24 may be removed from the receptacle 22 in order to obtain a specimen of the discharge.

The determined peak flow rate of the discharge may be utilized to initially screen patients into a normal or abnormal category relative to voiding capability. Since the velocity of the urine discharge is dependent upon the anatomical location of a possible stricture impeding discharge by the patient, the data associated with the peak flow rate and velocity of the discharge may be further utilized to determine the relative location of the obstruction in the patient which impedes voiding.

The foregoing detailed description is given for clearness of understanding only, and no unnecessary limitations should be understood therefrom, as modifications will be obvious to those skilled in the art.

I claim:

1. A device for measuring a urine discharge, comprising: a hollow receptacle having an inlet port adjacent an upper end of the receptacle and channel means below the inlet port to receive the liquid passing through the inlet port, a paddle assembly rotatably mounted on the receptacle and having rotatable blade means located in the path of said discharge, and means responsive to the rate of rotation of the paddle assembly for measuring the velocity of said discharge passing from the port to the channel means, including means for measuring and recording the maximum velocity of said discharge passing from the port to the channel means.

2. The device of claim 1 wherein the paddle assembly further comprises, a shaft, a plurality of elongated blades spaced circumferentially around the shaft and extending radially from the shaft, and means for rotatably supporting said shaft on the receptacle with an outer end portion of the blades located in the path of the discharge intermediate the port and channel means, and in which the velocity measuring means comprises means for generating a signal responsive to rotation of said shaft, and means for measuring said signal.

3. The device of claim 2 wherein the generating means comprises a generator connected to said shaft.

4. The device of claim 3 wherein the signal measuring means comprises an ammeter.

5. The device of claim 1 wherein the paddle assembly has a plurality of blades rotatably mounted on the receptacle with an outer end portion of the blades located in the path of the discharge.

6. A device for measuring a urine discharge, comprising: a hollow receptacle having a sidewall defining inlet port means adjacent an upper end of the receptacle, channel means below the inlet port means to receive the discharge passing through the port means, a paddle assembly received in a back portion of said sidewall, said assembly having a rotatable shaft, and a plurality of elongated blades spaced circumferentially around the shaft and having outer end portions located in the path of said discharge, means for generating a signal responsive to the rate of rotation of said shaft and the velocity of said discharge, means for measuring said signal to determine the velocity of the discharge, and means for measuring the peak flow rate of the discharge, with said channel means directing the discharge to the flow rate measuring means.

7. The device of claim 6 wherein a portion of said paddle assembly is located outside said sidewall, and including a cover for said outer portion of the paddle assembly.

8. The device of claim 6 including means for releasably attaching the paddle assembly to the back portion of said sidewall.

9. A device for measuring a urine discharge, comprising:
   a hollow receptacle having a sidewall defining inlet port means adjacent an upper end of the receptacle, with a back portion of the sidewall having a cutout, and channel means below the inlet port means to receive the discharge passing through the port means;

a paddle assembly comprising, a housing having a back cover member defining a cavity, and a front opening, a shaft rotatably supported in the housing cavity, and a plurality of elongated blades extending radially from and spaced circumferentially around the shaft in said cavity with outer end portions of the blades projecting out of the housing opening when aligned with said opening;

means for supporting said housing in said sidewall cutout with said projecting blade end portions located in the path of the discharge;

means for generating a signal responsive to rotation of said blades and shaft; and means for measuring said signal.

10. A device for measuring a urine discharge, comprising:

a hollow receptacle having a sidewall defining inlet port means adjacent an upper end of the receptacle, with a back portion of the sidewall having a cutout, and channel means below the inlet port means to receive the discharge passing through the port means;

a paddle assembly comprising, a housing having a back cover member defining a cavity, and a front opening, a shaft rotatably supported in the housing cavity, and a plurality of elongated blades extending radially from and spaced circumferentially around the shaft in said cavity with outer end portions of the blades projecting out of the housing opening when aligned with said opening;

means for supporting said housing in said sidewall cutout with said projecting blade end portions located in the.path of the discharge, comprising slot means extending around the sides and lower front part of the housing to receive an edge portion of the sidewall extending around said cutout;

means for generating a signal responsive to rotation of said blades and shaft; and means for measuring said signal.

11. A device for measuring both the velocity and flow rate of a single urine discharge, comprising:

a hollow receptacle;

liquid velocity measuring means for measuring the velocity of a single urine discharge passing into said receptacle without significantly affecting the flow rate of said discharge;

liquid flow rate measuring means for separately measuring the flow rate of said single urine discharge after it passes from said liquid velocity measuring means; and means for directing the urine discharge from the velocity measuring means to the flow rate measuring means.

12. A device as claimed in claim 11, further comprising:

liquid volume measuring means for measuring the volume of said single urine discharge after it passes from said liquid flow rate measuring means.

13. A device for measuring both the velocity and flow rate of a single urine discharge, comprising:

a hollow receptacle;

liquid velocity measuring means mounted on said receptacle for measuring the velocity of a single urine discharge passing into said receptacle without significantly affecting the flow rate of said discharge, said liquid velocity measuring means comprising a paddle assembly having a rotatable shaft with a plurality of blades mounted thereon with the end portions thereof located in the path of said discharge and signal generating means for generating a signal proportional to the speed of rotation of said shaft; and liquid flow rate measuring means mounted in said receptacle for separately measuring the flow rate of said single urine discharge after it passes from said liquid velocity measuring means, said liquid flow rate measuring means having liquid flow restriction means producing a liquid height in said receptacle proportional to said flow rate and indicating means for measuring said liquid height to indicate said flow rate.

* * * * *